United States Patent [19]
Paul et al.

[11] Patent Number: 5,158,535
[45] Date of Patent: Oct. 27, 1992

[54] CURVED TAMPON APPLICATOR AND A PROCESS FOR FORMING THE APPLICATOR AND FOR ASSEMBLING AN ABSORBENT TAMPON INTO SAID APPLICATOR

[75] Inventors: Susan C. Paul, Alpharetta, Ga.; Donald A. Sheldon, Appleton, Wis.

[73] Assignee: Kimberly-Clark Corporation, Neenah, Wis.

[21] Appl. No.: 537,677

[22] Filed: Jun. 14, 1990

Related U.S. Application Data

[63] Continuation-in-part of Ser. No. 855,048, Apr. 23, 1986, abandoned.

[51] Int. Cl.$^5$ .................... A61F 13/20; A61B 17/43; A61D 19/02
[52] U.S. Cl. ........................................ 604/15; 604/11; 604/904
[58] Field of Search ........................ 604/11–18, 604/904

[56] References Cited

U.S. PATENT DOCUMENTS

| | | | |
|---|---|---|---|
| 1,224,735 | 5/1917 | Gamache et al. | 604/15 |
| 2,386,590 | 10/1945 | Calhain | 604/15 |
| 2,879,770 | 3/1959 | Graham, Jr. | 128/263 |
| 3,063,453 | 11/1962 | Brecht | 128/285 |
| 3,643,661 | 2/1972 | Crockford | 604/15 |
| 3,765,417 | 10/1973 | Crockford | 604/15 |
| 3,807,399 | 4/1974 | Morman et al. | 128/263 |
| 3,835,856 | 9/1974 | Warncke | 604/15 |
| 4,269,187 | 5/1981 | Sakurai et al. | 128/263 |
| 4,276,881 | 7/1981 | Lilaonitkul | 128/263 |
| 4,332,251 | 6/1982 | Thompson | 128/263 |
| 4,361,150 | 11/1982 | Voss | 128/263 |
| 4,411,647 | 10/1983 | Sakurai et al. | 604/16 |
| 4,412,833 | 11/1983 | Wiegner et al. | 604/14 |
| 4,424,054 | 1/1984 | Conn et al. | 604/11 |
| 4,522,967 | 6/1985 | Sheldon et al. | 524/377 |
| 4,536,178 | 8/1985 | Lichstein et al. | 604/15 |
| 4,543,086 | 9/1985 | Johnson | 604/11 |
| 4,676,773 | 6/1987 | Sheldon | 604/16 |
| 5,061,274 | 10/1991 | Kensey | 604/15 X |

FOREIGN PATENT DOCUMENTS

WO84/04667 12/1984 World Int. Prop. O.

Primary Examiner—David Isabella
Assistant Examiner—Elizabeth M. Burke
Attorney, Agent, or Firm—Thomas J. Connelly

[57] ABSTRACT

A curved tampon applicator and a process for forming the applicator and assembling an absorbent tampon into the applicator is disclosed. The curved tampon applicator can facilitate placement of an absorbent tampon into a woman's vagina. The curved tampon applicator contains first and second arcuately shaped tubular members telescopically joined together. The first member has a stepped outer configuration with an enlarged portion designed to contain an absorbent tampon joined to a finger-grip portion. The enlarged portion is formed on a centerline having a first radius of curvature. The second member is formed on a centerline having a radius of curvature which is different from the first radius of curvature. The second member is sized and configured to slide within the finger-grip portion while being restricted from rotating therein. The second member contains at least one flared end which is sized to prevent separation of the second member from the first member. The flared end is initially positioned within the enlarged portion of the first member and is designed to push the absorbent tampon out of the first member when the second member is moved into the first member.

18 Claims, 3 Drawing Sheets

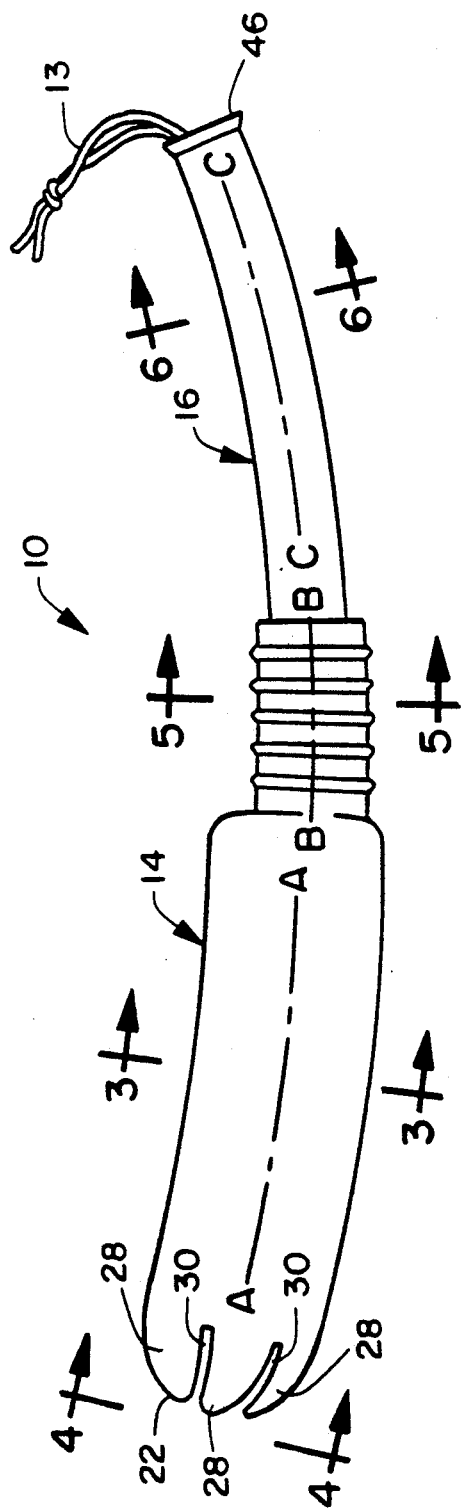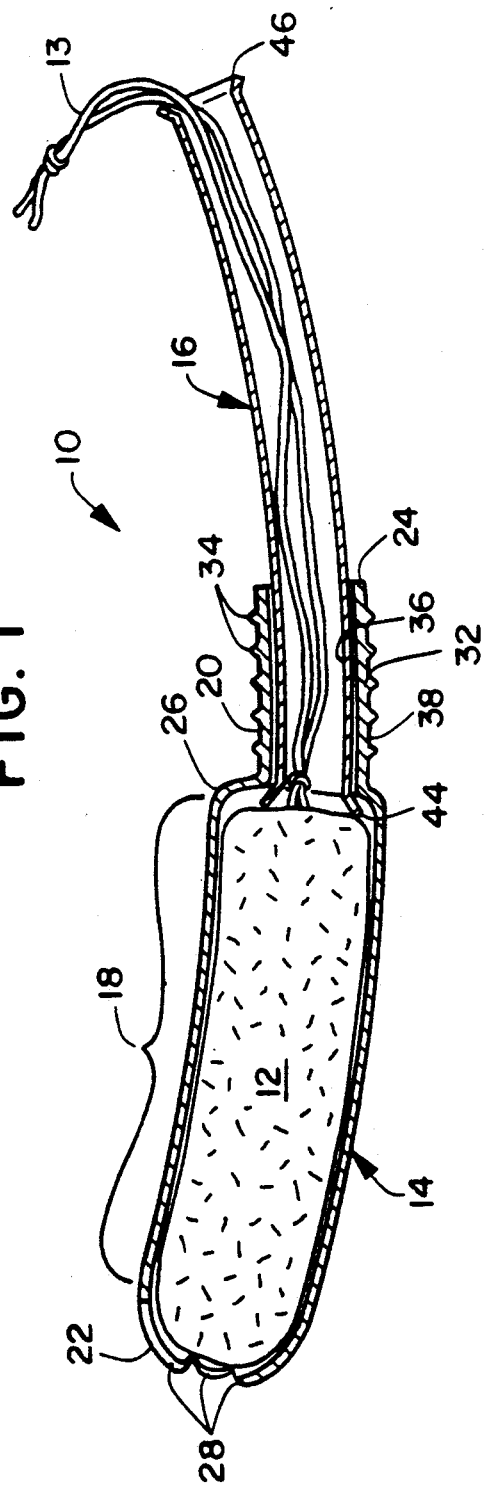

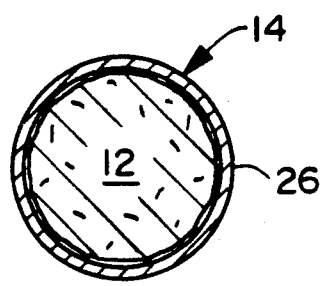
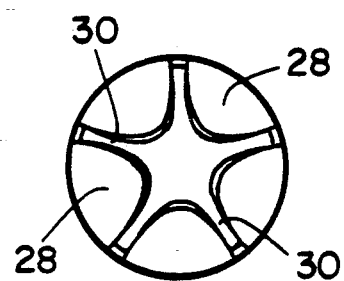
FIG. 3                FIG. 4
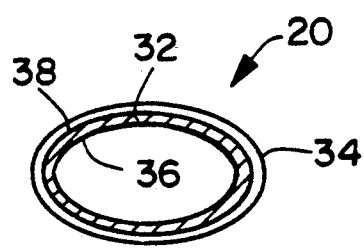
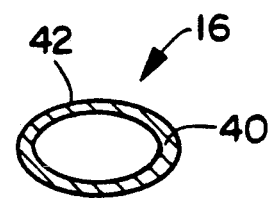
FIG. 5                FIG. 6

CURVED TAMPON APPLICATOR AND A PROCESS FOR FORMING THE APPLICATOR AND FOR ASSEMBLING AN ABSORBENT TAMPON INTO SAID APPLICATOR

This application is a continuation-in-part of U.S. application Ser. No. 06/855,048 filed Apr. 23, 1986 now abandoned.

FIELD OF THE INVENTION

This invention relates to a curved tampon applicator which can facilitate placement of a catamenial tampon into a woman's vagina. More particularly, it relates to a process for forming the applicator by combining arcuately shaped inner and outer telescoping tubes, each having a predetermined radius of curvature, and by positioning an absorbent tampon in the outer tube.

BACKGROUND OF THE INVENTION

There are a variety of tampon applicators available today for catamenial purposes. Many of these tampon applicators utilize telescoping inner and outer members in which the outer member is a hollow tube which is adapted to contain a tampon and the inner member is a push rod used to expel the tampon from the outer tube. The push rod may be in the form of a solid paper stick or a hollow tube having a diameter slightly less than that of the outer tube. Essentially, all of the tampon applicators sold today have a longitudinally straight axis.

U.S. Pat. No. 3,765,417 issued to Crockford, and assigned to the present assignee, teaches a tampon applicator having inner and outer telescoping members each having an arc of the same radius. The radius is in the range of about 4 to 6 inches. However, the applicator does not contain petals on the leading end of the outer member. A sharp radius of curvature in combination with petals can cause discomfort during insertion of the applicator into a woman's vagina as well as during the expulsion of the tampon from the applicator. Such pinching normally occurs once the tampon is ejected from the outer tube and the petals start to close. This pinching of the flesh can be painful and is unacceptable to the ultimate consumer.

Other patents which teach tampon applicators having a curved outer tube include: German patents 423,181; 241,771 and 96,307. However, none of these patents teach the use of petals on the leading end of the outer member. Another patent WO 84/04667, issued to Fournier, teaches an applicator for veterinarian use. The applicator has a shape and length adapted to the morphology of the animal species. The applicator utilizes a curved outer tube having essentially a constant outside diameter. The leading end of the outer tube is round and contains slits which form an even number of lugs. There is no mention of a particular radius of curvature but, by taking a measurement of the arc shown in FIG. 1 of the drawings, a radius of curvature of approximately 5.375 inches is obtained. This radius is substantially less than that used in the present invention. It should also be noted that the vaginal cavity of an animal differs from a woman's in both shape and length. This is emphasized on page 2, lines 14-16 of the patient wherein it is stated that "the physiology and anaotomy of animals are totally different from those of women." Accordingly, this sharp radius of curvature, along with petals formed on the leading end of the outer member, most likely would be unacceptable to most women. Unlike animals, women do have the ability to purchase a different applicator if they experience any pain or discomfort while positioning a tampon into their vagina.

Other U.S. patents which describe straight versus curved tampon applicators, but which teach some of the other features disclosed in the present invention, such as a gripping means, a reduced cross-sectional area on the outer tube, an odd number of petals, etc. include: U.S. Pat. Nos. 3,807,399; 4,269,187; 4,332,251; 4,361,150; 4,412,833; 4,424,054 and 4,536,178. Lastly, U.S. Pat. Nos. 2,879,770 and 3,063,453 teach catemenial tampons which exhibit a curved profile once the tampon has been ejected from a straight applicator.

Now a curved tampon applicator has been developed which makes it easier for a woman to insert an absorbent tampon into her vagina.

SUMMARY OF THE INVENTION

Briefly, the preset invention relates to a curved tampon applicator which can facilitate placement of an absorbent tampon into a woman's vagina. A process for forming the curved tampon applicator and for assembling an absorbent tampon into the applicator is also disclosed. The curved tampon applicator contains first and second arcuately shaped tubular members telescopically joined together. The first tube has a stepped outer configuration with an enlarged portion designed to contain an absorbent tampon joined to a smaller finger-grip portion. The enlarged portion is formed on a centering having a first degree of curvature. The second tube is formed on a centerline having a second degree of curvature which is different from said enlarged portion. The second tube is sized and configured to slide within the finger-grip portion without easily being rotatable therein. The second tube contains at least one flared end which is sized to prevent separation of the second tube from the first tube. The flared end is initially positioned within the enlarged portion of the first tube and is designed to push the absorbent tampon out of the first tube when the second tube is moved into the first tube.

A process for forming the applicator and for assembling an absorbent tampon into the applicator is also disclosed.

The general object of this invention is to provide a curved tampon applicator which will facilitate placement to an absorbent tampon into a woman's vagina. A more specific object of this invention is to provide a curved tampon applicator which is easier to use than the traditional straight tampon applicators.

Another object of this invention is to provide a curved tampon applicator which can be easily used by both right-handed and left-handed women.

A further object of this invention is to provide a curved tampon applicator which utilizes an offset finger-grip portion to facilitate insertion of an absorbent tampon into a woman's vagina when the women is either sitting or standing.

Still another object of this invention is to provide a curved tampon applicator wherein the outer tube is constructed with a different degree of curvature than the inner tube so as to facilitate insertion of an absorbent tampon into a woman's vagina.

Still further, an object of this invention is to go against the teaching of the prior art for the last fifty years and produce a curved tampon applicator which is more comfortable for women to use rather than the conventional straight tampon applicator.

Other objects and advantages of the present invention will become more apparent to those skilled in the art in view of the following description and the accompanying drawings.

BRIEF DESCRIPTION OF THE DRAWINGS

FIG. 1 is a side elevational view of a curved tampon applicator for facilitating insertion of an absorbent tampon into a woman's vagina.

FIG. 2 is a cross-sectional view of the curved tampon applicator shown in FIG. 1 depicting an absorbent tampon positioned in the outer tube.

FIG. 3 is a cross-sectional view of the outer tube taken along line 3—3 of FIG. 1.

FIG. 4 is an end view of the enlarged portion of the outer tube taken along line 4—4 of FIG. 1.

FIG. 5 is a cross-sectional view of the finger-grip portion taken along line 5—5 of FIG. 1.

FIG. 6 is a cross-sectional view of the inner tube taken along line 6—6 of FIG. 1;

DETAILED DESCRIPTION OF THE PREFERRED EMBODIMENTS

Figure 7:
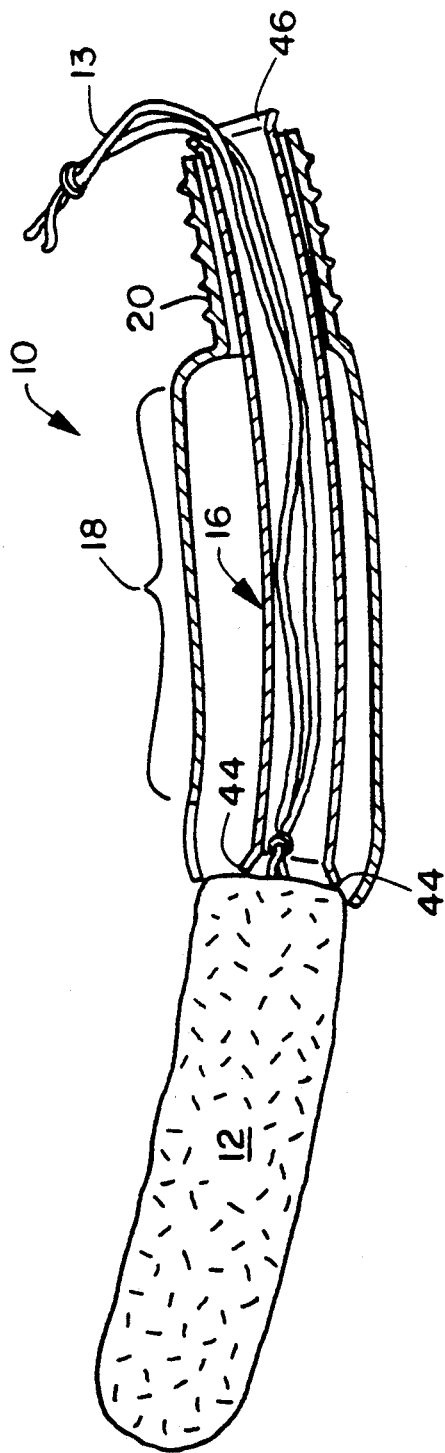
FIG. 7 is a sectional view of the curved tampon applicator in a portion where the tampon has been ejected from the outer tube.

Referring to FIGS. 1 and 2, a curved tampon applicator 10 is shown containing a catamenial tampon 12. The catamenial tampon 12 has an attached withdrawal string 13 and is intended to be inserted into a woman's vagina during her menstrual period to block the flow of menstrual fluid, blood, etc. therefrom.

The curved tampon applicator 10 includes a first member 14 and a second member 16. The first member 14 is a hollow tube about 2 to 3 inches long and has a diameter of about ¼ to ¾ of an inch. Preferably, the first member or outer tube 14 is made out of low density polyethylene which can be injection molded. However, the curved tampon applicator 10 can be constructed out of one or more layers of paper or cardboard, or it can be made from one or more types of thermoplastic materials. It is also possible to construct one of the members out of paper and form the other member out of a thermoplastic material. Water dispersible, water-soluble, photodegradable and biodegradable materials should be utilized when possible.

The outer tube 14 has an arcuate shape with a centerline A—A formed on an arc having a predetermined radius of curvature. The arc can be formed with a radius of curvature of between about 6 to 10 inches, preferably between about 7 and 9 inches, and most preferably, about 8 inches. An arc having a certain radius of curvature is equivalent to an arcuate segment of a circle having a given radius. The outer tube 14 has a stepped outer configuration with an enlarged portion 18, designed to hold the absorbent tampon 12, joined to a smaller finger-grip portion 20. The outer tube 14 also contains first and second distally spaced end 22 and 24, respectively.

The enlarged portion 18 of the outer tube 14 has a generally circular or round cross-section, as is shown in FIG. 3, and is sized to be slightly larger than the outside diameter of the absorbent tampon 12, which it is designed to contain. The enlarged portion 18 has a wall 26 which tapers in thickness as it approaches the first end 22. The difference in wall thickness is beneficial in that it permits petals 28, see FIG. 4, to be formed approximate the first end 22. The petals 28 are thin, flexible members separated by slots or grooves 30. The petals 28 are capable of bending radially outward as the absorbent tampon 12 is expelled from the curved tampon applicator 10. A plurality of petals 28, preferably an odd number, such as 3, 5, 7 etc. should be utilized because an odd number of petals 28 will prevent the outer tube 14 from collapsing or flattening after the tampon 12 has been expelled. By preventing the outer tube 14 from collapsing, one can be assured that the vaginal tissue will not be pinched. This will assure safe use of the product and will contribute to additional sales of the curved tampon applicator 10.

Referring to FIGS. 1, 2, 5 and 7, the finger-grip portion 20 of the outer tube 14 is shown having elliptical or oval cross-sectional shape and is formed on a centerline B—B which is offset from the centerline A—A of the enlarged portion 18. The radius of curvature of the centerline B—B can be and most likely will be different from the radius of curvature of the centerline A—A. Preferably, the internal radius of curvature of the finger-grip portion 20 will be generally the same as the radius of curvature of the inner tube 16. In FIGS. 2 and 7, the internal radius of curvature of the finger-grip portion 20 is shown to be different from that of the inner tube 16 simply for the sake of distinguishing the two parts. The relatively flat surfaces of the oval are aligned generally parallel to the inner and outer peripheral walls of the enlarged portion 18 and thereby correspond to the upper and lower surfaces of the tampon applicator 10 as is depicted in FIGS. 1 and 2. The non-circular configuration of the finger-grip portion 20 makes it easier for a woman to hold the applicator 10. The particular orientation of the applicator 10 can vary depending upon what feels best for each individual. The offset of the finger-grip portion 20 is toward the longer surface (the longer peripheral wall) of the enlarged portion 18, as is shown in FIG. 2. The finger-grip portion 20 also has a greater degree of curvature than the enlarged portion 18. The combustion of the offset and the greater degree of curvature contribute to produce a curved tampon applicator 10 which is easier to handle. The offset further enables the applicator 10 to have more of a curve without the need to increase the degree of curvature of the enlarged portion 18. The comfort level of using a curved tampon applicator may diminish when the curvature of the enlarged portion 18 of the outer tube 14 is too drastic and when petals are formed on the insertion end 22. When the radius of curvature of the outer tube 14 is less than about 6 inches, the petals 28 can cause pinching or scratching of the vaginal tissue during either insertion of the applicator into the vagina or after the expulsion of the tampon 12 from the applicator.

It should be noted that a tubular member formed on an arc having a large radius of curvature is equivalent to a member having a smaller degree of curvature. The offset of the finger-grip portion 20 gives the curved tampon applicator 10 the appearance of having a greater degree of curvature while utilizing a very gentle curvature for the enlarged portion 18 of the outer tube 14. This combination also aids in the aesthetic and visual appearance of the curved tampon applicator 10.

The finger-grip portion 20 contains a peripheral wall 32 which has one or more ribs or protrusions 34 formed about the exterior thereof. The ribs 34 provide a gripping surface to assist the user in holding the curved tampon applicator 10 between her thumb and middle finger. Her index finger is used to push the second member or inner tube 16 into the outer tube 14 and thereby expel the absorbent tampon 12. The curved tampon applicator 10 can easily be handled with one hand. Other known types of gripping means can also be used. Such means include score lines, ridges, rings, dimples, a roughened surface, or by applying a covering or coating having a high coefficient of friction. It should be pointed out that the finger-grip portion 20 is designed to be comfortable to both right-handed and left-handed women.

Referring to FIG. 5, the finger-grip portion 20 contains an interior and an exterior surface, 36 and 38 respectively, both of which have an oval profile. The oval should be an ellipse of between about 15° and 45°. An ellipse of about 30° provides a good gripping surface and adds strength to the outer tube 14. An ellipse formed between about 15° and 45° would have a cross-section which would appear similar to that of a circle which has been turned between about 15° and 45° to a viewer's eye. The offset of the finger-grip portion 20 from the enlarged portion 18 in combination with the elliptical profile allows a woman to use the applicator 10 to insert the tampon 12 while she is sitting, standing with one leg raised or while lying on her back. This is an improvement over straight tampon applicators which can be difficult to handle in certain positions.

Referring to FIGS. 1, 2 and 6, the second member or inner tube 16 is shown partly positioned within the finger-grip portion 20 of the outer tube 14. The second member 16 is a hollow tube, preferably made out of high density polyethylene, which can be extruded. The inner tube 16 has an arcuate shape with a centerline C—C formed on an arc having a predetermined degree of curvature. The arc can be formed with a radius of curvature of between about 6 to 10 inches, preferably between about 6 and 8 inches; and most preferably below 7.5 inches. The radius of curvature of the inner tube 16 is different from that of the outer tube 14. Preferably, the radius of curvature of the inner tube 16 will be slightly less than that of the outer tube 14. For example, when the outer tube 14 has a radius of curvature of about 8 inches, the radius of curvature of the inner tube 16 will be about 7 to 7.5 inches. Since the inner tube 16 has a smaller radius of curvature, it will have a greater degree of curvature than the outer tube 14 and, therefore, will exhibit a greater amount of curvature. This extra amount of curvature is beneficial when a woman goes to position the tampon applicator 10 into her vagina, and it also facilitate expulsion of the absorbent tampon 12 from the applicator 10.

The inner tube 16 has a wall 40 which has an exterior, ovalshaped surface 42. The wall 40 is about 0.01 to 0.02 inches thick and is thinner than the wall of the finger-grip portion 20 which can be around 0.035 inches thick. The exterior surface 42 is sized and configured to mate with and be slidable with the interior surface 36 of the finger-grip portion 20. The oval configuration permits the inner and outer tubes, 14 and 16 respectively, to move in a telescoping fashion while preventing the inner tube 16 from rotating relative to the outer tube 14.

This is important because the inner tube 16 is designed to push the absorbent tampon 12 out of the enlarged portion 18 of the outer tube 14. If rotation was allowed, the inner tube 16 could bind up in the finger-grip portion 20 or rub against the inner wall of the outer tube 14 and be prevented from expelling the tampon 12.

The inner tube 16 also contains first and second spaced-apart ends 44 and 46. At least one, and preferably both, of the ends 44 and 46 are flared after the inner tube 16 has been inserted into the outer tube 14. The amount of flare can vary depending upon the dimensions of the inner and outer tubes, 14 and 16 respectively, and the diameter of the tampon 12 which is to be ejected. For ease of manufacture, the inner tube 16 should be made slightly longer in length than the outer tube 14. This difference in length will facilitate flaring of the ends 44 and 46 and will also provide assurance that the inner tube 16 has sufficient length to expel the tampon 12 from the outer tube 14.

Referring to FIG. 7, the curved tampon applicator 10 is shown in a position where the inner tube 16 has been pushed almost completely into the outer tube 14 and the flared end 44 has pushed the absorbent tampon 12 completely out of the enlarged portion 18. The flared end 46 on the opposite end of the inner tube 16 will restrict the travel of the inner tube 16 into the outer tube 14. At this point, the user would withdraw the two coaxially aligned tubes 14 and 16. In doing so, the free end of the withdrawal string 13 will slide through the central opening of the inner tube 16 and be will available for removal of the tampon from the woman's vagina.

Figure 9:
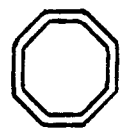
FIG. 9 is an alternative embodiment showing a finger-grip portion with an octagon configuration.
Figure 8:
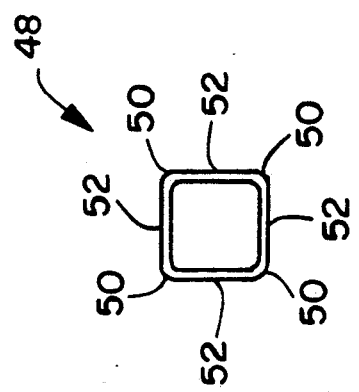
FIG. 8 is an alternative embodiment showing a finger-grip portion with a four-sided exterior configuration with rounded corners.

Referring to FIGS. 8 and 9, two alternative embodiments are depicted for the exterior surface of the finger-grip portion 20. In FIG. 8, a four-sided tubular member 48 is shown having rounded corners 50 formed between the adjacent flat sides 52. The tubular member 48 can be either a square or a rectangle. In FIG. 9, an eight-sided tubular member 54 is shown having the shape of an octagon. The octagon can have equal or different length sides. It should be noted that other shapes, including polygon shapes can be utilized. The purpose of making the exterior surface of the finger-grip portion 20 in the shape of a four, five, six, seven or an eight-sided member is to make the curved tampon applicator 10 easier to handle. The presence of relatively flat sides provides handles for the user's finger tips. The presence of horizontal or vertical surfaces, as well as diagonal surfaces in the case of the octagon profile, gives the user a wide variety of discretion as to how to position the curved tampon applicator 10 for the upmost comfort during insertion of the absorbent tampon 12.

Figure 10:
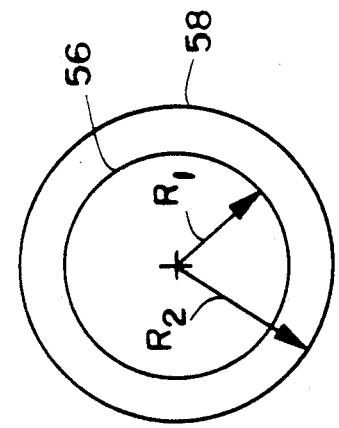
FIG. 10 shows two circles having different radiuses of curvature.

FIG. 10 shows two circles 56 and 58 having radiuses $R_1$ and $R_2$. Circle 56 has a smaller radius of curvature $R_1$ but a greater degree of curvature then the circle 58 which has a larger radius of curvature $R_2$.

Although several specific materials have been mentioned as being suitable for forming the inner and outer tubes, 14 and 16 respectively, it should be noted that many other material can also be utilized. The material should be strong enough to support the gripping and expulsion activities of the applicator 10. Plastic materials are preferred because of their smooth feel. Typical plastic which can be used include: polyethylene, polystyrene, polypropylene and acrylonitrile-butadiene-styrene resins. A preferred material is low density or linear low-density polyethylene for it is easy to mold into thin-walled tubes and is low in cost. It should be remembered that the two tubes 14 and 16 can be made out of different materials. In the event that a flushable applicator is desired, a cardboard convolutely wound tube held together by a water-soluble adhesive can be constructed. Such a tube is taught in U.S. Pat. No. 4,522,967 issued to Sheldon et al. and assigned to the present assignee. This patent is incorporated by reference and made a part hereof.

The absorbent tampon 12 shown in FIGS. 2 and 7 can be of any suitable construction and can be either straight or curved. The tampon 12 can have a bullet shape or rounded insertion and instead of a blunt end if this is desired. The tampon 12 can also be preformed as a straight member but have enough resiliency to acquire an arcuate profile after it is positioned in the enlarged portion 18 of the outer tube 14 for a sufficient period of time. U.S. patent application Ser. No. 07/406,655 filed Sep. 12, 1989, entitled "An Apparatus And A Method For Forming Tampons And The Tampon Itself" and assigned to the present assignee teaches a tampon which can be used in the curved tampon applicator 10. This patent application is incorporated by reference and made a part hereof.

PROCESS

The curved tampon applicator 10 can be formed in a number of different ways. A preferred method is to injection mold the outer tube 14 from a thermoplastic resin, such as low density polyethylene into an arcuate shape having a predetermined degree of curvature. The outer tube 14 should have a stepped outer configuration with an enlarged portion 18 joined to a finger-grip portion 20. Preferably, the finger-grip portion 20 is offset from the arcuate centerline of the enlarged portion 18. The offset should be towards the longer surface of the outer tube 14 as explained above. The petals 28 can be formed on the insertion end 22 of the outer tube 14 when the tube 14 is molded. Likewise, the ribs 34 formed on the exterior surface of the finger-grip portion 20 can be formed during the molding process.

The inner tube 16 can be extruded from a thermoplastic resin such as high-density polyethylene in the form of a straight tube having relatively constant dimensions. The straight tube 16 can then be heat formed or heat seat into an arcuate shape having a degree of curvature which is greater than that of the outer tube 14. One method of heat setting the inner tube 16 is to immerse it into a bath of hot water for a sufficient period of time. It should be pointed out that certain extruded thermoplastics have a memory and, therefore, they will revert back to their initial extruded shape over a period of time or at elevated temperatures. This factor should be kept in mind if extrusion is contemplated. The inner tube 16 can also be injection molded if desired.

After the outer and inner tubes, 14 and 16 respectively, are formed, one end of the inner tube 16 is inserted in to and through the outer tube 14. It is important to make the inner tube 16 slightly longer in length that the outer tube 14, for this will facilitate flaring of the ends 44 and 46 of the inner tube 16 once the two tubes are assembled. As noted above, either one or both ends of the inner tube 16 can be flared so as to prevent the two tubes from separating from one another. Numerous methods for flaring paper or plastic tubes are known in the art and equipment is commercially available for performing this task.

After the inner tube 16 has been inserted into the outer tube 14, the absorbent tampon 12 is positioned into the enlarged portion 18 via the first end 22. The petals 28 are spread apart and the absorbent tampon 12 is inserted with the withdrawal string 13 positioned adjacent to the second end 24 of the outer tube 14. The withdrawal string 13 can be guided, such as by a vacuum, down through the finger-grip portion 20 and through the central opening in the inner tube 16. The free end of the withdrawal string 13 should extend out beyond the second end 46 of the inner tube 16, as is clearly shown in FIGS. 1 and 2. The visual presence of the withdrawal string 13 will give the ultimate user assurance that the tampon 12 does have a withdrawal string 13 attached thereto.

While the invention has been described in conjunction with several specific embodiment, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:
1. A curved tampon applicator comprising:
   a) a first member having an arcuate shape and having a stepped outer configuration with an enlarged portion formed with a predetermined degree of curvature which is designed to contain an absorbent tampon joined to a smaller tubular finger-grip portion; and
   b) a second member having an arcuate shape formed with a different degree of curvature than said first member, said first and second members being joined together to enable said members to telescopically move relative to one another and having means for resisting rotation relative to one another, said second member having at least one flared end which is sized to prevent separation of said second member from said first member, said flared end initially being positioned within said enlarged portion and designed to push said absorbent tampon out of said first member when said second member is moved into said first member.
2. The curved tampon applicator of claim 1 wherein said second member has an oval, cross-sectional shape and a greater degree of curvature than said first member.
3. The curved tampon applicator of claim 2 wherein both said first and second members are formed with an arc having a radius of curvature greater than 6 inches.
4. The curved tampon applicator of claim 1 wherein said finger-grip portion is offset from a centerline extending along a length of said enlarged portion, said finger-grip portion facilitating positioning of said applicator into a woman's vagina.
5. The curved tampon applicator of claim 4 wherein said finger-grip portion is formed on an arc having a greater degree of curvature than an arc on whcih said enlarged portion is formed.
6. A curved tampon applicator comprising:
   a) a first member having an arcuate shape and having a stepped outer configuration with an enlarged portion designed to contain a tampon joined to a smaller tubular finger-grip portion, said enlarged portion having a centerline formed on an arc having a first radius of curvature, said stepped configuration having first and second ends;
   b) petals formed on said first end of said first member, said petals capable of being deflected outwardly to permit said tampon to be ejected from said first member; and c) a second member having an arcuate shape with a centerline formed on an arc having a radius of curvature which is different from said first radius of curvature, said first and second members being telescopically joined together, said second member being sized and configured to slide within said finger-grip portion and having means for resisting rotation therein, said second member having first and second flared ends which are sized to prevent separation of said second member from said first member, said first flared end being initially positioned within said enlarged portion of said first member and designed to push said tampon out of said first member when said second member is moved into said first member.

7. The curved tampon applicator of claim 6 wherein said second member has a greater degree of curvature than said first member.

8. The curved tampon applicator of claim 7 wherein both said first and second members are formed on arcs having a radius of curvature greater than 6 inches.

9. The curved tampon applicator of claim 6 wherein said finger-grip portion has an elliptical cross-sectional shape and is offset from the centerline of said enlarged portion which has a circular cross-sectional shape.

10. The curved tampon applicator of claim 9 wherein said finger-grip portion has at least two flat external surfaces which are aligned perpendicular to the radius of curvature of said outer tube.

11. The curved tampon applicator of claim 6 wherein said second member has a non-circular cross-sectional configuration.

12. The curved tampon applicator of claim 11 wherein said second member has an external profile containing at least four sides with rounded corners formed therebetween.

13. The curved tampon applicator of claim 12 wherein said second member has an external profile in a shape of a polygon.

14. A curved tampon applicator for facilitating placement of an catamenial tampon into a woman's vagina, comprising:

a) a first member having an arcuate shape and having a stepped outer configuration with an enlarged circular cross-sectional portion designed to contain an absorbent tampon joined to a smaller oval cross-sectional finger-grip portion, said enlarged portion having a centerline formed on an arc having a first radius of curvature, said finger-grip portion being offset from said enlarged portion, said stepped configuration having first and second ends;

b) a plurality of petals formed on said first end of said first member, said petals capable of being deflected radially outward to permit said absorbent tampon to be ejected from said first member, and c) a second member having an arcuate shape with a centerline formed on an arc having a radius of curvature which is greater than said first radius of curvature, said first and second members being telescopically joined together, said second member having an oval cross-sectional shape and being sized to slide within said finger-grip portion while being restricted from rotating therein, said second member having first and second flared ends whcih are sized to prevent separation of said second member from said first member, said first flared end being initially positioned within said circular portion of said first member and designed to push said absorbent tampon from said first member when said second member is moved into said first member.

15. The curved tampon applicator of claim 14 wherein said second member is longer than said first member.

16. The curved tampon applicator of claim 14 wherein said enlarged portion of said first member has a thin wall which tapers in thickness from an end adjacent to said finger-grip portion down toward said first end.

17. The curved tampon applicator of claim 14 wherein said finger-grip portion has an oval shaped interior surface which is equal in size to an exterior surface of said oval cross-sectional shaped second member.

18. The curved tampon applicator of claim 14 wherein said finger-grip portion has a wall thickness which is greater than a wall thickness of said second member.

* * * * *

UNITED STATES PATENT AND TRADEMARK OFFICE
CERTIFICATE OF CORRECTION

PATENT NO. : 5,158,535

DATED : October 27, 1992

INVENTOR(S) : Susan C. Paul; Donald A. Sheldon

It is certified that error appears in the above-identified patent and that said Letters Patent is hereby corrected as shown below:

Column 2, line 47, delete the word "to" and substitute therefor --of--.

Column 2, line 57, delete the word "women" and substitute therefor --woman--.

Column 3, line 22, delete the word "portion" and substitute therefor --position--.

Column 6, line 50, delete the word "upmost" and substitute therefor --utmost--.

Column 7, line 11, delete the word "and" and substitute therefor --end--.

Column 7, line 44, delete the word "seat" and substitute therefor --set--.

Column 8, line 14, delete the word "embodiment" and substitute therefor --embodiments--.

UNITED STATES PATENT AND TRADEMARK OFFICE
CERTIFICATE OF CORRECTION

PATENT NO. : 5,158,535
DATED : October 27, 1992
INVENTOR(S) : Susan C. Paul, et. al.

It is certified that error appears in the above-indentified patent and that said Letters Patent is hereby corrected as shown below:

Column 10, Claim 14, line 22, delete the word "whcih" and substitute therefo --which--.

Signed and Sealed this

Nineteenth Day of October, 1993

Attest:

BRUCE LEHMAN

*Attesting Officer*  *Commissioner of Patents and Trademarks*